US008639467B2

(12) United States Patent
Michael et al.

(10) Patent No.: US 8,639,467 B2
(45) Date of Patent: Jan. 28, 2014

(54) MEASURING SYSTEM FOR DETERMINING A VALUE OF A PHYSICAL OR CHEMICAL, MEASURED VARIABLE OF A MEDIUM AND METHOD FOR OPERATION OF THE MEASURING SYSTEM

(75) Inventors: Ronny Michael, Erlau OT Crossen (DE); Hermann Gunther, Dresden (DE); Sven-Matthias Scheibe, Dresden (DE); Hendrik Zeun, Chemnitz (DE)

(73) Assignee: Endress + Hauser Conducta Gesellschaft für Mess- und Regeltechnik mbH + Co. KG, Gerlingen (DE)

(*) Notice: Subject to any disclaimer, the term of this patent is extended or adjusted under 35 U.S.C. 154(b) by 475 days.

(21) Appl. No.: 12/971,190

(22) Filed: Dec. 17, 2010

(65) Prior Publication Data

US 2011/0153259 A1   Jun. 23, 2011

(30) Foreign Application Priority Data

Dec. 23, 2009 (DE) .......................... 10 2009 055 231

(51) Int. Cl.
*G06F 19/00* (2011.01)
*G05B 21/00* (2006.01)

(52) U.S. Cl.
USPC .......................................... 702/123; 700/266

(58) Field of Classification Search
USPC ................... 702/123, 1–2, 22–25, 30–32, 57,
702/64–65, 85, 104, 127, 188–189;
700/266–267; 340/3.1, 3.3, 3.31–3.32
See application file for complete search history.

(56) References Cited

U.S. PATENT DOCUMENTS

| 6,285,964 | B1* | 9/2001 | Babel et al. | 702/121 |
| 7,785,151 | B2* | 8/2010 | Feucht et al. | 439/660 |
| 2010/0312491 | A1* | 12/2010 | Lohmann et al. | 702/31 |

FOREIGN PATENT DOCUMENTS

DE   10218606 A1 * 11/2003

* cited by examiner

*Primary Examiner* — Toan Le
(74) *Attorney, Agent, or Firm* — Bacon & Thomas, PLLC

(57) ABSTRACT

A measuring system for determining a value of a physical or chemical, measured variable of a medium, includes: a base unit; at least one relay unit connected with the base unit and a sensor unit connected with the relay unit. The sensor unit includes a circuit having at least one microcontroller, at least a first memory region, and a second memory region. The upload software is embodied, in interaction with the microcontroller, to perform an updating of the basic software with at least one software module provided from the base unit. The relay unit includes a circuit having at least one microcontroller, and at least a first memory region, in which a basic software of the relay unit is stored. The circuit of the relay unit further includes a second memory region, in which an upload software of the relay unit is stored.

10 Claims, 3 Drawing Sheets

MEASURING SYSTEM FOR DETERMINING A VALUE OF A PHYSICAL OR CHEMICAL, MEASURED VARIABLE OF A MEDIUM AND METHOD FOR OPERATION OF THE MEASURING SYSTEM

TECHNICAL FIELD

The invention relates to a measuring system for determining a value of a physical or chemical, measured variable of a medium, wherein the measuring system includes a base unit, at least one relay unit connected with the base unit and a sensor unit connected with the relay unit, wherein the relay unit is especially embodied to receive, and to forward to the sensor unit, data sent from the base unit, especially measurement data, operating data, commands or software modules, and/or to receive, and to forward to the base unit, data sent from the sensor unit, especially measurement data, operating data, commands or software modules.

BACKGROUND DISCUSSION

Such measuring systems are applied frequently in industrial, process measurements technology for determining values of physical and of chemical, measured variables, especially pH value, conductivity, turbidity, concentration of one or more substances, especially certain ions, such as ammonium and nitrate, or dissolved gases, as e.g. $CO_2$ or $O_2$, in a measured medium. Such measuring systems are especially also applied in connection with the automation of chemical or manufacturing processes and/or the automated control of industrial plants.

The sensor unit can be, for example, an electrochemical probe, especially a potentiometric or amperometric probe. Examples of potentiometric sensor types are ion selective electrodes, such as e.g. a glass electrode for measuring pH value. An example of an amperometric sensor type is a dissolved oxygen sensor working according to the principle of the Clark electrode. The sensor unit can also be a conductivity probe immersible in the medium and working according to a conductive or inductive measuring principle or an optical probe immersible in the medium, for example, for measuring turbidity according to the nephelometric or turbidimetric principle or for measuring of concentrations of certain substances, e.g. nitrate, absorbing at the wavelength of the optical probe.

For registering the respective measured variables, the sensor units have, in each case, a corresponding measuring transducer with a physical to electrical or chemical to electrical transducer, which outputs an electrical signal dependent on the value of the measured variable, as well as, connected to the measuring transducer, a circuit, as a rule, an electronic circuit, which serves for conditioning and, in given cases, further processing, the signals provided by the measuring transducer and for their forwarding to the base unit. The circuit includes for this at least one microcontroller and a data memory circuit, in which a basic software, also referred to as firmware, is stored, which provides basic functions required for processing the measuring signals. The base unit includes a data processing unit, which can process data received from the sensor unit and output the processed data via an interface to a display unit, e.g. a display, or to a superordinated unit, for example, a process control system. The base unit can be, for example, a measurement transmitter with input and display functions.

Data transmission between the sensor unit and the base unit can occur via a relay unit connected between the sensor unit and the base unit and embodied to forward, to the sensor unit, data sent from the base unit, especially measurement data, operating data, commands or software modules, and/or to forward, to the base unit, data sent from the sensor unit, especially measurement data, operating data, commands or software modules. Examples of measuring systems embodied in such a manner are described, for example, in DE 102 18 606 A1 or DE 10 2006 005633 A1. The relay unit includes in these measuring systems likewise a microcontroller, as well as at least one memory, in which is stored a basic software of the relay unit for providing the basic functionalities of the relay units. In the measuring systems described in DE 102 18 606 A1 and DE 10 2006 005633 A1, the sensor unit and the relay unit are connected releasably with one an additional via an inductively coupling, pluggable connector coupling.

In WO 2009/060001 A1, a measuring point for determining a value of a physical or chemical, measured variable of a medium is described, wherein the measuring point includes a base unit and a sensor unit, wherein the sensor unit is connectable releasably with the base unit via a pluggable connector coupling. The base unit is provided for energy supply of the sensor unit, for data exchange with the sensor unit and for communication to a process monitoring facility of a signal representing the value of the measured variable. It includes a first microprocessor for conditioning data received from the sensor unit, for communication to the process monitoring facility and a data memory for the storage of measuring point specific data. The sensor unit includes a primary sensor with a transducer, which outputs an electrical signal dependent on the value of the measured variable, and a circuit for conditioning the transducer signals, wherein the circuit includes an A/D converter and a second microprocessor for processing digitized signals and a data memory, in which sensor specific data are stored, as well as a program memory, which contains a low level software with basic functionalities for the operation of the sensor unit. Via an inductive interface, via which the energy supply of the sensor unit by the base unit and the data exchange with the base unit occurs, at least one software module is transmittable from the base unit to the sensor unit and storable in the program memory of the sensor unit, wherein the software module contains supplemental functions for monitoring the primary sensor. In this way, low level software stored in the program memory of the sensor unit can be updated.

In the case of the measuring systems known from the state of the art, it is, however, not provided, also to update a basic software, especially a low level, basic software, of the relay unit providing the basic functions of the relay unit.

SUMMARY OF THE INVENTION

An object of the invention is, consequently, to provide a measuring system of the previously described type, which permits both an updating of the basic software of the sensor unit, as well as also an updating of the basic software of the relay unit.

This object is achieved by a measuring system for determining a value of a physical or chemical, measured variable of a medium. The measuring system comprises a base unit, at least one relay unit connected with the base unit and a sensor unit connected with the relay unit, wherein the relay unit especially is embodied to receive from the base unit, and to forward to the sensor unit, data, especially measurement data, operating data, commands or software modules and/or to receive from the sensor unit, and to forward to the base unit, data, especially measurement data, operating data, commands or software modules, wherein the sensor unit comprises a circuit having:

at least one microcontroller;

at least a first memory region, especially a non volatile, first memory region, in which a basic software of the sensor unit is stored;

and a second memory region, especially a non volatile, second memory region, in which an upload software of the sensor unit is stored, wherein:

the upload software of the sensor unit is embodied, in interaction with the microcontroller, to perform an updating of the basic software of the sensor unit with at least one software module provided from the base unit and the relay unit comprises a circuit having: at least one microcontroller; and at least a first memory region, especially a non volatile, first memory region, in which a basic software of the relay unit is stored.

The circuit of the relay unit further comprises a second memory region, especially a non volatile, second memory region, in which an upload software of the relay unit is stored, which is embodied, in interaction with the microcontroller of the relay unit, to perform an updating of the basic software of the relay unit with at least one software module provided from the base unit, and the upload software of the sensor unit, for execution by the microcontroller of the sensor unit, is activatable based on a comparison of a data sequence sent from the base unit with a first password assigned to the sensor unit, especially a first password formed by a first data sequence and the upload software of the relay unit, for execution by the microcontroller of the relay unit, is activatable based on a comparison of a data sequence sent from the base unit with a second password assigned to the relay unit, especially a second password formed by a second data sequence, especially a second password different from the first password.

The basic software of the sensor unit provides basic functionalities of the sensor unit, especially functions for processing of measurement signals provided to the microcontroller by a measuring transducer, fed via an input stage to the microcontroller as digitized measurement data, or functions for performing sensor diagnostic methods. Especially, the basic software is a software conventionally also referred to as firmware, especially at least partially low level software. The first memory region, in which the basic software is stored, can be a non volatile memory, e.g. a PROM or an EPROM, of the circuit of the sensor unit. The basic software can be programmed in this memory persistently, in order, in given cases, to be loaded for the operation of the sensor unit into a volatile data memory, e.g. a RAM, serving as working memory. Persistent means here, that the basic software, on the one hand, also remains stored and, thus, performable after a restart of the microcomputer caused by interruption of the energy supply of the sensor unit, and that, on the additional hand, the basic software stored within the memory can be partially reprogrammed or even completely over written.

The basic software of the relay unit provides basic functionalities of the relay unit. As in the case of the basic software of the sensor unit, the basic software of the relay unit is an at least partially low level software, also referred to as firmware, stored persistently, in the previously described sense, in a second non volatile memory region of the circuit of the relay unit.

Since the relay unit and the sensor unit, in each case, has its own circuit with a memory region, in which, respectively, an upload software of the relay unit, and an upload software of the sensor unit, is stored, and these are activatable, in each case, for execution by the microcontroller of the sensor unit, or the relay unit, based on a comparison of a data sequence sent from the base unit with a first password assigned to the sensor unit, or a second password assigned to the relay unit, wherein the passwords differ especially from one another, so that an option is selectively to execute the upload software of the sensor unit, or that of the relay unit.

The base unit can thus selectively "choose" either the sensor unit or the relay unit for performing an updating, by sending to the relay unit a data sequence, which agrees with the password assigned to the unit to be selected. If the comparison of the data sequence with the password of the relay unit results in an agreement, the microcontroller of the relay unit activates the upload software stored in the second memory region of the relay unit for performing an updating of the basic software on the basis of at least one software module provided from the base unit. If the comparison, in contrast, results in no agreement, the upload software of the relay unit is not activated. Instead, the microcontroller of the relay unit, in this case, executes the basic software of the relay unit, in order to receive data from the base unit and to forward such to the sensor unit and/or to receive data from the sensor unit, and to forward such to the base unit. Correspondingly, in this case, also the data sequence sent from the base unit is forwarded to the sensor unit. If the comparison of the data sequence sent from the base unit with the password of the sensor unit results in an agreement, the microcontroller of the sensor unit activates the upload software stored in the second memory region of the sensor unit for performing an updating of the basic software of the sensor unit using at least one software module provided from the base unit. If the comparison, in contrast, results in no agreement, the upload software of the sensor unit is not activated. Instead, the microcontroller of the sensor unit can then execute the basic software of the sensor unit.

The upload software of the relay unit and the upload software of the sensor unit can be embodied in association with the microcontroller of the relay unit, or of the sensor unit, as the case may be, such that at least one software module provided from the base unit is loaded first into a third, volatile or non volatile, memory region of the circuit of the sensor or relay unit, depending on whether the basic software of the sensor unit or that of the relay unit should be updated. When the loading of the software module provided from the base unit is finished flawlessly, the sensor unit, or the relay unit, as the case may be, can send a confirmation report back to the base unit. If the base unit receives no confirmation report within a predetermined time span, it sends the software module anew.

Following loading of the software module into the third memory region of the circuit, the parts of the version of the basic software previously stored in the first memory region to be changed in the context of the updating can be deleted and at least be replaced by parts of the software module located in the third memory region. It is also possible to completely write over the version previously stored in the first memory region, by deleting the entire basic software stored in the first memory region and writing a software module, as provided from the base unit and loaded in the third memory region of the unit to be updated, newly into the first memory region, so that the software module forms the new basic software of the unit, which was to be updated.

The upload software of the sensor unit and the upload software of the relay unit can be boot loaders, which are embodied, when activated for execution by the microcontroller of the sensor unit, or the relay unit, respectively, to set in motion a communication with the base unit and to load, provided from the base unit, especially sent thereby, software modules into the third memory region of the circuit of the sensor unit, or the relay unit, as the case may be.

In an additional embodiment, the first and the second password can supplementally to the verification the authorization of the base unit, serve for performing updates of the basic software of the sensor unit and/or the relay unit. By means of the password, it can, thus, be checked, whether the base unit has access rights to the upload software of the sensor unit, or the relay unit. Additionally, the password can also serve for encoding of software modules, which are sent from the base unit to the sensor unit or to the relay unit.

The circuit of the sensor unit includes, preferably, a non volatile data storage circuit serving for the persistent storage of software and having the earlier named, first memory region, second memory region and third memory region. Likewise, the circuit of the relay unit preferably includes a non volatile data storage circuit serving for the persistent storage of software and including the earlier named, first, second and third memory regions of the relay unit.

It is advantageous to assign to all sensor units of a certain sensor type or a certain product series the same password, especially when all sensor units of a product series can be operated with the same basic software version. In this way, sensor units of the same type can be inserted in place of one another, without having to report a new password to the base unit. Correspondingly, also the same password can be associated with all relay units of a certain type, especially a product series. The terminology, 'sensor units, or relay units of a type', means, especially, sensor units, or relay units, which have basic software with equal, or only slightly differing, basic functionalities.

The sensor unit can have a measuring transducer, which is contactable with the medium, and which outputs an electrical signal dependent on the value of the measured variable, wherein the circuit of the sensor unit includes an A/D converter for producing digital data from the electrical signal of the measuring transducer for processing by the microcontroller of the sensor unit. For example, the sensor unit can be an electrochemical probe, an optical probe or a conductivity measuring probe of the initially named type.

The measuring transducer can be connected fixedly with a first element of a pluggable connector coupling, in which the sensor circuit is accommodated. The relay unit can comprise a second element of the pluggable connector coupling, in which the circuit of the relay unit is accommodated, wherein, between the circuit of the sensor unit and the circuit of the relay unit, data and/or energy are exchangeable via the pluggable connector coupling, when the first and the second elements of the pluggable connector coupling are connected with one another. The pluggable connector coupling can be implemented by usual plug connectors with plug and socket, via which a galvanic connection is produced. Alternatively, the pluggable connector coupling can provide galvanic isolation between the sensor unit and the relay unit by transmitting data and/or energy via an inductive or optical coupling between the circuit of the sensor unit and the circuit of the relay unit.

The relay unit can be connected with the base unit by means of a cable connection. The base unit can be, for example, a measurement transmitter having a data processing unit, an input function for servicing by a service person and a display function.

The base unit can be connected with at least one additional relay unit, which is connected with an additional sensor unit, wherein the additional relay unit is embodied, especially, to forward to the sensor unit data received from the base unit, especially measurement data, operating data, commands or software modules, and to forward to the base unit data received from the sensor unit, especially measurement data, operating data, commands or software modules, wherein the additional sensor unit includes a circuit having a microcontroller, at least a first memory region, in which a basic software of the additional sensor unit is stored, and a second memory region, in which an upload software of the additional sensor unit is stored, which is embodied, in interaction with the microcontroller of the additional sensor unit, to perform an updating of the basic software of the additional sensor unit with software modules received from the base unit, and wherein the additional relay unit includes a circuit with a microcontroller, a first memory region, in which a basic software of the additional relay unit is stored, and a second memory region, in which an upload software of the additional relay unit is stored, which is embodied, in interaction with the microcontroller of the additional relay unit, to perform an updating of the basic software of the additional relay unit, and wherein the upload software of the additional sensor unit, for execution by the microcontroller of the additional sensor unit, is activatable based on a comparison of a data sequence sent from the base unit with a third password assigned to the additional sensor unit.

If the sensor unit and the additional sensor unit involve the same type of sensor units, for example, two pH sensor units of the same series, the passwords, by means of which the particular upload software of the sensor unit and the additional sensor unit are activatable, can be identical. If, however, the first sensor unit and the additional sensor unit involve different sensor units, for example, a pH sensor and a conductivity sensor, then different passwords are associated with them, by means of which the base unit can initiate an updating of the basic software of the first or the additional sensor unit.

In the previously described embodiment, the relay units can be embodied identically, and especially comprise the same basic functionalities, which are provided by identical versions of the basic software of the relay units. In this case, it is advantageous to activate the corresponding upload software of each relay unit by means of the same password, in order to obtain execution by the microcontroller of the respective relay unit. In this case, the same password can be assigned to the relay units, so that the upload software of the relay unit, for execution by the microcontroller of the relay unit and the upload software of the additional relay unit, for execution by the microcontroller of the additional relay unit, especially are activatable simultaneously, based on one and the same data sequence sent from the base unit.

The invention includes also a method for the operation of a measuring system for determining a value of a physical or chemical, measured variable of a medium, especially to start up or updating of the measuring system, wherein the measuring system includes a base unit and at least one relay unit connected with the base unit and a sensor unit connected with the relay unit, wherein the relay unit is embodied, especially, to receive from the base unit, and to forward to the sensor unit, data, especially measurement data, operating data, commands or software modules, and/or to receive from the sensor unit, and to forward to the base unit, data, especially measurement data, operating data, commands or software modules, wherein the base unit, for initiating an updating of basic software of the sensor unit stored in a first memory region of the sensor unit or basic software of the relay unit stored in a first memory region of the relay unit sends to the relay unit a data sequence forming a password, wherein a microcontroller of the relay unit compares the data sequence with a password assigned to the relay unit, and in case the data sequence agrees with the password assigned to the relay unit, activates an upload software stored in a second memory region of the relay unit for performing an updating of the basic software of the relay unit, or, in case the data sequence does not agree with the password assigned to the relay unit, by means of a function provided by the basic software of the relay unit, forwards the data sequence to the sensor unit;

and wherein, in case the relay unit forwards the data sequence to the sensor unit, a microcontroller of the sensor unit compares the data sequence with a password assigned to the sensor unit, and in case the data sequence agrees with the password assigned to the sensor unit, activates an upload software stored in a second memory region of the sensor unit for performing an updating of the basic software of the sensor unit.

The microcontroller of the sensor unit can, in case the data sequence does not agree with the password assigned to the sensor unit, execute the basic software of the sensor unit, especially in order to register, in given cases, to process and transmit to the relay unit, at least one measured value of the physical or chemical, measured variable.

To the extent that the upload software of one of the units, i.e. the sensor unit or the relay unit, is not activated, these transfer into their basic function operation, whose functionalities the particular basic software makes available. To the extent that the upload software of the sensor unit is activated, the upload software of the relay unit remains inactive, since the sensor unit and the relay unit have different passwords. Thus, during the updating of the basic software of the sensor unit, the relay unit remains in its basic function, i.e. it serves for forwarding data sent from the base unit to the sensor unit, especially data in the form of a software module sent from the base unit for storing by the upload software in a memory region of the software unit. To the extent that the upload software of the relay unit is activated, the sensor unit remains in its basic functionality, i.e. it continues to register measured values, while the basic software of the relay unit is being updated. In this way, the basic software of the sensor unit and the basic software of the relay unit can be selectively updated.

The base unit can, for updating the basic software of the relay unit, transmit at least one software module to the relay unit, wherein the microcontroller of the relay unit executes the activated upload software, in order to load the software module received from the base unit at least partially into a third memory region of the relay unit and/or in order to write the software module received from the base unit at least partially into the first memory region of the relay unit, in which the basic software of the relay unit is stored, especially with write over of at least one part of the stored basic software, in order to update the basic software of the relay unit.

The base unit can, for updating the basic software of the sensor unit, transmit at least one software module via the relay unit to the sensor unit, wherein the microcontroller of the sensor unit executes the activated upload software, in order to load the software module received from the base unit at least partially into a third memory region of the sensor unit and/or in order to write the software module received from the base unit at least partially into the first memory region of the sensor unit, in which the basic software of the sensor unit is stored, especially with write over of at least one part of the stored basic software, in order to update the basic software of the sensor unit.

When the loading of the software module sent from the base unit to the sensor unit or to the relay unit is flawlessly finished, the sensor unit, or the relay unit, can send a confirmation report back to the base unit. If the base unit receives within a predetermined time span no confirmation signal, it sends the software module anew.

The here described method can be applied, for example, at start up of the sensor unit. Start up of the sensor unit can especially comprise connecting the sensor unit to the relay unit. For this, the sensor unit can have a first element of a pluggable connector coupling, in which the sensor circuit is accommodated. The relay unit can correspondingly comprise a second element of the pluggable connector coupling, in which the circuit of the relay unit is accommodated. By connecting the two elements of the pluggable connector coupling, an interface is formed for transmission of data and/or energy between the sensor unit and the relay unit. If the sensor unit of the base unit is supplied via the relay unit and the pluggable connector coupling with energy, the microcontroller of the sensor unit can be started up following the connecting of the pluggable connector coupling. In case the microcontroller of the sensor unit receives the password assigned to the sensor unit within a predetermined time span following the starting up of the base unit, it can activate the upload software in such a manner, that it is executable by means of the microcomputer, in order to perform an updating of the basic software of the sensor unit, or, in case the microcontroller of the sensor unit receives no data sequence forwarded from the base unit via the relay unit within the predetermined time span in agreement with the password assigned to the sensor unit, the microcontroller of the sensor unit can activate the basic software stored in the first memory region of the sensor unit in such a manner, that it is executable by means of the microcontroller of the relay unit, in order to derive from a signal supplied to the microcontroller via an A/D converter from a measuring transducer of the sensor unit a measured value and to transmit such to the relay unit. This corresponds to the basic function operation of the sensor unit.

In the case of start up of the sensor unit, especially directly following connecting of the sensor unit to the relay unit, the microcontroller of the relay unit can likewise be newly started up. This can, for example, occur by having the base unit interrupt the energy supply of the microcontroller of the sensor unit for a short time, such that it is, thereafter, brought back. In case the microcontroller of the relay unit receives within a predetermined time span following the starting up of the base unit a data sequence, which agrees with the password assigned to the relay unit, the microcontroller can activate the upload software stored in the second memory region of the relay unit in such a manner, that it is executable by means of the microcontroller, in order to perform an updating of the basic software of the relay unit, or the microcontroller can, in case it receives from the base unit within the predetermined time span no data sequence, which agrees with the password assigned to the relay unit, activate the basic software stored in the first memory region of the relay unit in such a manner, that it is executable by means of the microcontroller, in order to forward to the sensor unit received data from the base unit, especially measurement data, operating data, commands or software modules and/or to forward to the base unit data received from the sensor unit, especially measurement data, operating data, commands or software modules. This corresponds to the basic function operation of the relay unit.

At start up of the sensor unit, especially directly following connecting of the sensor unit to the relay unit, the sensor unit can transmit to the relay unit, for forwarding to the base unit, data, which comprise information concerning the sensor unit, especially concerning the type of the measuring transducer of the sensor unit, the type of the sensor unit and/or the version of the basic software stored currently in the first memory region of the sensor unit.

In an alternative method variant, the updating of the basic software of the relay unit and/or the sensor unit can also be initiated by an input of a service person to an input function of the base unit, such that, upon the input, the base unit starts up the microcontroller of the sensor unit and/or the microcontroller of the relay unit anew, e.g. by short term interrupting, and, thereafter, bringing back, of the energy supply of the sensor unit and/or of the relay unit and, as earlier described, sending a data sequence to the relay unit and/or to the base unit for initiating the updating. In case the relay unit within a predetermined time span receives the password assigned to the relay unit, the microcontroller of the relay unit can activate the upload software for updating the basic software of the relay unit. Otherwise, the microcontroller activates the basic software of the relay unit, such that it transfers into basic function operation. The relay unit then, in basic function operation, forwards to the sensor unit the data sequence sent from the base unit. If the microcontroller receives within a predetermined time span the password assigned to the sensor unit, the microcontroller of the sensor unit can activate the upload software for updating the basic software of the sensor unit. Otherwise, the sensor unit transfers into its basic function operation.

BRIEF DESCRIPTION OF THE DRAWINGS

Other features, opportunities for application and advantages the invention will become evident from the following description of examples of embodiments of the invention. The figures of the drawing show as follows.

DETAILED DISCUSSION IN CONJUNCTION WITH THE DRAWINGS

Figure 1:
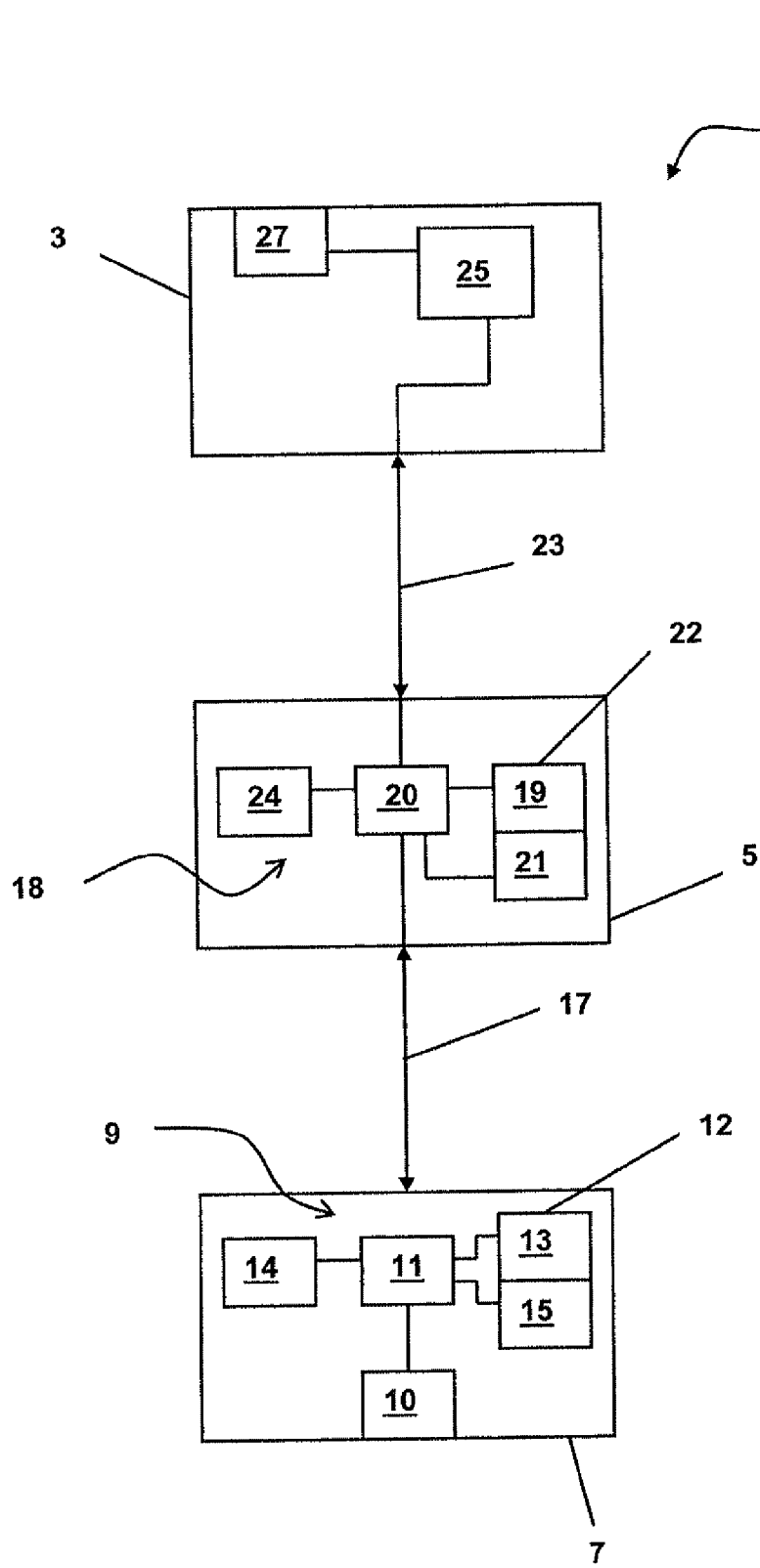
FIG. 1 is a schematic representation of a measuring system having a base unit, a relay unit and a sensor unit.

FIG. 1 shows schematically a measuring system 1 having a base unit 3, a sensor unit 7 and, interposed between the sensor unit 7 and the base unit 3, a relay unit 5.

Sensor unit 7 includes a measuring transducer 10, which is contactable with the medium, whose physical or chemical property is to be measured. Measuring transducer 10 includes a physical to electrical or chemical to electrical transducer, which outputs an analog electrical signal dependent on the value of the measured variable. The measuring transducer 10 can be, for example, a pH single rod measuring chain, also referred to as a pH glass electrode, which transduces the current pH value of the measured medium into a potential difference between a reference potential and a pH dependent potential. Alternatively, the measuring transducer 10 can comprise as transducer an inductive conductivity measurement arrangement, which detects by means of a second receiver coil an electrical current induced in the measured medium by a first, electrical current bearing coil and outputs as signal a voltage, or electrical current, dependent on the conductivity of the measured medium. An option is also an embodiment of the measuring transducer 10 as an amperometric measuring arrangement, which outputs an electrical current level dependent on the concentration of a gas dissolved in the measured medium, a gas such as, for example, $O_2$ or $CO_2$. Other embodiments of the measuring transducer 10 are thinkable, especially for measuring mass flow, density, viscosity, volume flow, flow velocity, pressure, temperature or turbidity.

The sensor unit 7 can be embodied as a probe, which extends at least partially into a container, which contains the measured medium, for example, a pipeline, a flume, a tank or a vat, so that the transducer comes in sufficient contact with the medium for performing measurements. The sensor unit 7 includes for the internal further processing of the measurement signal output by the measuring transducer a circuit 9, which includes at least one microcontroller 11. The, as a rule, analog, measurement signal output by the measuring transducer is fed to the microcontroller 11 via an input stage, which includes an analog/digital transducer, which converts analog measurement signals into digital measurement data.

The software required for operation of the microcontroller 11, especially a basic software providing the basic functionalities of the sensor unit 7, is at least partially stored in a first memory region 13 of a non volatile data memory circuit 12, to which the microcontroller 11 has at least data reading and also data writing access. The data storage circuit 12 can, for example, be implemented by means of an EEPROM circuit or by means of a plurality of modular EEPROM circuits. The circuit 9 includes furthermore a volatile data storage circuit 14 serving as working memory, which is formed, for example, by static and/or dynamic RAM circuits. Furthermore, the data memory circuit 12 includes a second memory region 15, in which an upload software is stored, which is embodied, in interaction with the microcontroller 11, to perform an updating of the basic software of the sensor unit 7 with application of at least one software module provided from the base unit 3. The microcontroller 11 can, thus, by executing the upload software, for example, perform a reconfiguring or an upgrade of the basic software of the sensor unit 5 stored in the first memory region 13.

Sensor unit 7 is connected with the relay unit 5 via an interface 17. Interface 17 can transmit data and/or energy in both directions. Interface 17 can be embodied, for example, as a pluggable connector coupling, which will be more exactly explored in connection with FIG. 2. The relay unit 5 is connected via an additional interface 23, especially via a cable, with the base unit 3. Also, via the additional interface 23, data and/or energy are transmittable in both directions. Thus, the sensor unit 7 and the relay unit 5 can be supplied with energy from the base unit 3 and/or exchange data with the base unit 3.

Relay unit 5 includes a circuit 18, which includes at least one microcontroller 20 and a non volatile data memory circuit 22. The data memory circuit 22 includes a first memory region 19, in which a basic software of the relay unit 5 is stored, especially persistently. The microcontroller 20 has data reading and data writing access to the first memory region 19. The basic software of the relay unit 5 provides basic functionalities of the relay unit 5, especially functions for the receipt of data from the sensor unit 7 and for forwarding this data to the base unit 3, as well as for the receipt of data from the base unit 3 and for forwarding this data to the sensor unit 7. Furthermore, the data memory circuit 22 includes an additional memory region 21, in which an upload software of the relay unit 5 is stored persistently. This upload software is embodied, in interaction with the microcontroller 20, to perform an updating of the basic software of the relay unit 5 using at least one provided software module by the base unit 3. The microcontroller 20 can, thus, by executing the upload software, for example, perform a reconfiguring or an upgrading of the basic software of the sensor unit 5 stored in the first memory region 19 of the relay unit. The non volatile data storage circuit 22 can be implemented, for example, by means of an EEPROM circuit or by means of a plurality of modular EEPROM circuits. Circuit 18 includes, furthermore, a volatile data storage circuit 24 serving as working memory, which is formed, for example, by static and/or dynamic RAM circuits.

Base unit 3 includes a data processing unit 25, especially a computer, which can process data received from the sensor unit 7 via the relay unit 5, especially measurement data, operating data or commands. The data processing unit 25 is, furthermore, embodied to transmit measurement data, operating data, commands or software modules to the relay unit 5, or via the relay unit 5 to the sensor unit 7. The base unit 3 includes, furthermore, an interface 27 for the connection of a semiconductor memory, especially an EEPROM/flash memory, in which software modules, for example, one or more versions of a basic software of the base unit 3, one or more versions of the basic software of the relay unit 5 or one or more versions of the basic software of the sensor unit 7 are stored. The corresponding software versions can be read out by the base unit from the EEPROM/flash memory and stored in a memory of the base unit 3. Interface 27 is, for example, embodied as a USB interface. Interface 27 can, alternatively or supplementally, provide an interface to a superordinated control unit, for example, a process control station, in order to permit bidirectional communication between the base unit 3 and the superordinated control unit. Preferably, such an interface is of type RS485.

In order to perform an updating of the basic software of the sensor unit 7 stored in the first memory region 13 of the sensor unit 7, the base unit 3 can transmit one or more software modules via the interface 23 to the relay unit 5 and via the interface 17 to the sensor unit 7. The microcontroller 11 executes the upload software stored in the second memory region 15, in order to load the transmitted software modules first into the working memory 14 of the sensor unit 7 and to write it persistently into the first memory region 13 of the data storage circuit 12. In given cases, outdated software modules of the original basic software are deleted from the data storage unit 13 or over written. This is also referred to as reconfiguration, or upgrading. An updating of the basic software of the relay unit 5 stored in the first memory region 19 of the relay unit 5 occurs analogously, such that the base unit 3 sends one or more software modules via the interface 23 to the relay unit 5. The microcontroller 20 executes the upload software stored in the second memory region 19, in order to load the transmitted software modules first into the working memory 24 of the relay unit 5, and then these are written persistently into the first memory region 19 of the relay unit 5.

When the loading of the software module sent from the base unit 3 to the sensor unit 7 or to the relay unit 5 is finished flawlessly, the sensor unit 7, or the relay unit 5, as the case may be, can send a confirmation report back to the base unit 3. If the base unit 3 receives no confirmation signal within a predetermined time span, it sends the software module anew.

Since the basic software of the sensor unit 7 and the basic software of the relay unit 5 provide different functionalities, the upload software of the sensor unit 7 is only activated, when the base unit 3 provides sensor modules for updating basic software of the sensor unit 7. Correspondingly, the upload software of the relay unit 5 is only activated, when the base unit 3 provides sensor modules for updating the basic software of the relay unit 5.

For this purpose, the base unit 3 addresses that unit, whose basic software is to be updated. This occurs by means of an addressing on the basis of a password formed, for example, by a data sequence, in each case, unequivocally associated with the sensor unit 7, or the relay unit 5, as the case may be. This data sequence can be placed in front of the sending of a software module from the base unit 3. Only when the relay unit 5 or the sensor unit 7 receives its assigned password, is the corresponding upload software activated. When the non-selected unit fails to receive its assigned password, it transfers into its basic operating mode. The basic operating mode of the sensor unit 7 is the registering, processing and/or forwarding of signals of the transducer 10. The basic operating mode of the relay unit 5 is the forwarding to the base unit 3 of data received from the sensor unit 7, or the forwarding to the sensor unit 7 of data received from the base unit 3.

A reconfiguration of the basic software of the relay unit, or the sensor unit 7, can be performed, for example, at start up of the measuring system 1. Start up of the measuring system 1 comprises connecting a new sensor unit 7 to the relay unit 5 via the interface 17. By connecting the sensor unit 7 with the relay unit 5, the sensor unit 7 is supplied with energy from the base unit 3 via the relay unit 5 and the interface 17, so that the microcontroller 11 can be started up. At start up or following start up, the microcontroller 11 can transmit to the base unit 3 information stored in the data memory circuit 12 of the sensor unit 7 concerning sensor type of the sensor unit 7 and concerning version of the basic software stored in the first memory region 13. Thereupon, the base unit 3 can test, whether the type and the version of the present basic software is still current, or whether they must be updated, for example, when, in the memory of the base unit, a more up to date version of the basic software is present. An updating can especially be required, when the basic software of the sensor unit 7 is not compatible or only partially compatible with the software of the base unit 3. A reconfiguration can also be required, for example, when newer versions of the software are present or when for the particular application, i.e. for the particular application of the measuring system 1, particular supplementing software modules are required for the basic software. The base unit 3 can hold ready, current software versions, or measuring point specific software modules, in a memory, or can load these via the interface 27 from a connected flash memory or from a superordinated unit connected via the interface 27.

If an updating of the basic software of the sensor unit 7 is required, the base unit 3 starts the microcontroller 20 of the relay unit 5 and the microcontroller 11 of the sensor unit anew, for example, by interrupting their energy supply for a short time. The base unit 3 then sends via the interface 23 to the relay unit 5, firstly, a data sequence forming the password assigned to the sensor unit 7 and, secondly, the software modules required for the updating. The microcontroller 20 of the relay unit 5 compares, following the start up, the data sequence received from the base unit 3 with a password stored in the data memory circuit 22 of the relay unit 5. Since the password assigned to the sensor unit 7 differs from the password assigned to the relay unit 5, the comparison shows no agreement. The microcontroller 20 of the relay unit 5, thus, does not recognize the data sequence, and, thus, does not activate the upload software stored in the second memory region 21 of the relay unit 5. When the microcontroller 20 of the relay unit 5 receives within a predetermined time span from the base unit no data sequence, which agrees with the stored password, microcontroller 20 activates the basic software of the, so that relay unit 5 transfers into its basic function mode, i.e. it forwards the data sequence received from the base unit 3 and likewise received software modules from the base unit 3 via the interface 17 to the sensor unit 7.

The microcontroller 11 of the sensor unit 7 compares the data sequence forwarded by the relay unit 5 with a password stored in a memory region of the data memory circuit 12 of the sensor unit 7 and detects, based on this comparison, the data sequence as the password assigned to the sensor unit 7. On the basis of the established agreement, microcontroller 11 activates the upload software stored in the second memory region 15 of the data memory circuit 12 of the sensor unit 7. The microcontroller executes the activated upload software in the above related manner, in order to perform an updating of the basic software stored in the first memory region 13. After performing the updating, the microcontroller 11 activates the updated basic software stored in the first memory region 13 of the sensor unit 7, and so transfers into the basic function mode.

Should, correspondingly, an updating of the relay unit 5 be performed, the base unit 3 transmits via the interface 23 to the relay unit 5, following start up of the microcontrollers 20 and 11 of the sensor unit 7 and the relay unit 5, firstly, a data sequence corresponding to the password assigned to the relay unit 5 and, secondly, the software modules correspondingly needed for the updating. Upon receipt of the password assigned to the relay unit 5, microcomputer 18, based on a comparison of the received data sequence with the password stored in a memory region of the data memory circuit 22 of the relay unit 5, activates the upload software stored in the second memory region 21 for execution. The updating is performed as previously explained. If the sensor unit does not, within a predetermined time span, receive from the base unit 3 a data sequence corresponding to the password assigned to it, its microcontroller 11 activates its basic software, so that the sensor unit 7 transfers into its basic function mode.

The passwords assigned to the sensor unit 7 and to the relay unit 5, respectively, can simultaneously be used for controlling access rights to the upload software of the sensor unit, or the relay unit. Furthermore, a password can be used to encrypt the software modules sent together with the password. The transmission of one and the same password for these different tasks is especially resource saving. This increases also the processing speed, especially in the case of access activation.

Figure 2:
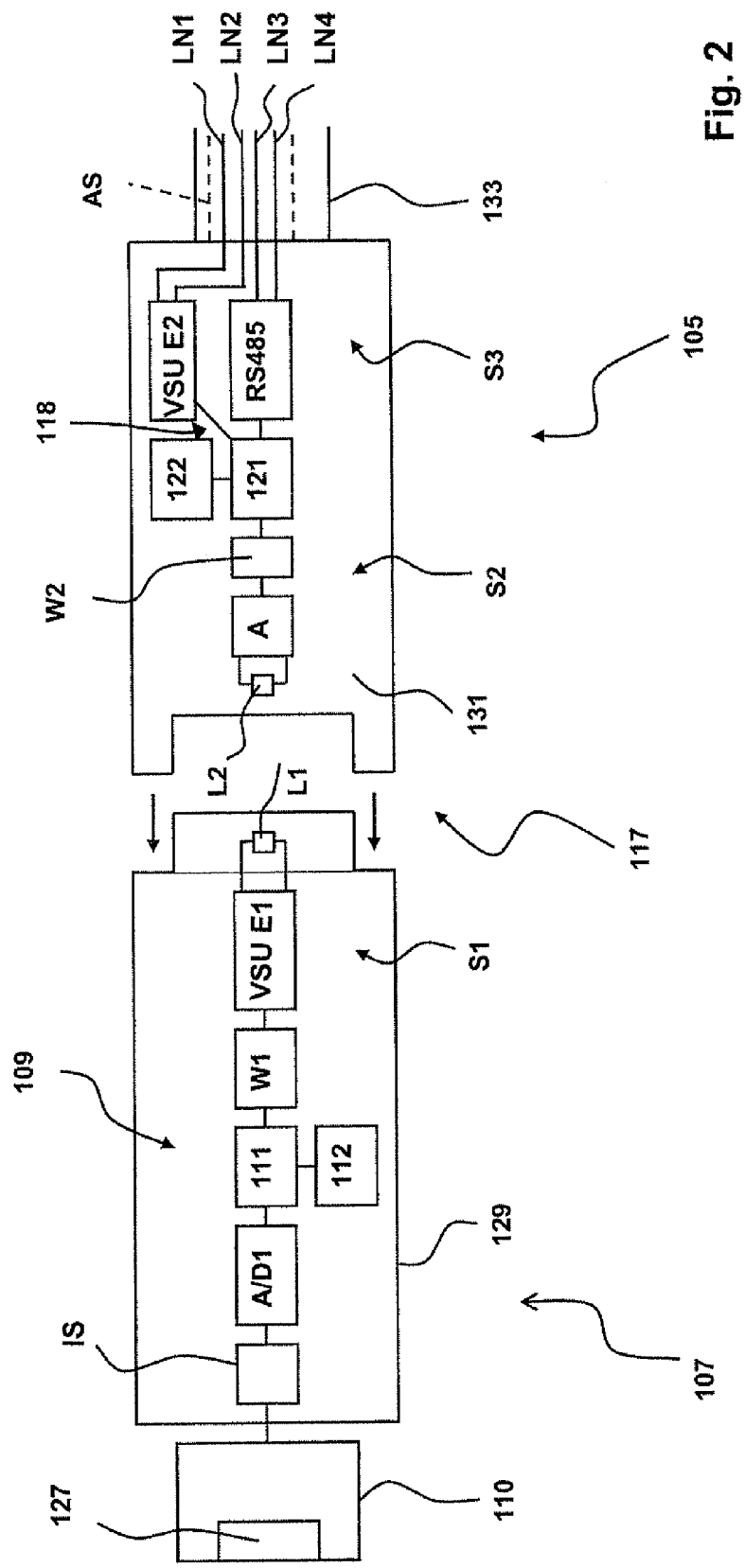
FIG. 2 is a schematic representation of a sensor unit and a relay unit connectable with the sensor unit.

FIG. 2 shows a schematic representation of a sensor unit 107 having a measuring transducer 110, and a plug head 129 connected fixedly with the measuring transducer 110. The plug head 129 forms a first element of a pluggable connector coupling, whose second element is formed by a plug head counterpart 131. The plug head 129 and the plug head counterpart 131 are connectable with one another, for example, via a bayonet connection.

Measuring transducer 110 includes a physical to electrical, or chemical to electrical, measuring transducer 127, which outputs, dependent on the measured variable, an electrical signal, which is output by the measuring transducer as an analog measurement signal. For transmission of the analog measurement signal output by the measuring transducer 110 to the microcontroller 111 accommodated in the plug head 129, the circuit 109 of the sensor unit 107 accommodated in the plug head 129 includes, besides the microcontroller 111, an input stage 1S, in which the analog measurement signal is preprocessed, for example, filtered or amplified, and fed via an analog/digital converter A/D1 as digital measurement data to the microcontroller 111. The basic software of the sensor unit 107, which provides, especially, basic functionalities for the additional processing of the measurement data by the microcontroller 111, is stored in a first memory region of a data storage circuit 112, which the microcontroller 111 can access, in order to load at least parts of the basic software into a volatile working memory of the microcontroller 111. Via a communication interface S1, the microcontroller 111 can transmit and receive data. Communication interface S1 is composed of a converter W1 and a coil L1 as well as an optional voltage supply unit VSU1.

The relay unit 105, which is embodied to receive data from the sensor unit 107 and to forward data to a base unit (not shown), as well as to receive data from the base unit and to forward data to the sensor unit 107, is formed in the example of FIG. 2 by the sensor head counterpart 131. Plug head counterpart 131 includes an interface, the communication interface S2, complementary to the communication interface S1. Interface S2 includes a coil L2, an optional amplifier A and a converter W2. When the sensor unit 107 and the relay unit 105 are connected with one another via the communication interfaces S1 and S2, data and energy transmission between the sensor unit 107 and the relay unit 105 in the two directions is possible.

The communication interface S2 of the relay unit is connected with a circuit 118 of the relay unit 105. Circuit 118 includes a microcontroller 121. The communication, i.e. the bidirectional data transmission with the base unit, occurs hardwired via a communication interface S3 of the relay unit 105, which is composed, for example, of a RS485 chip. Cable 133, which connects the sensor head counterpart 131 with the base unit, includes four lines LN1, LN2, LN3 and LN4, which are surrounded by a shielding SR Two of these lines serve for communication, while the two additional lines serve for energy transmission between the base unit and the plug head counterpart 131. Serving for energy supply of the plug head counterpart 131 is a voltage supply unit VSU2, which is supplied from the base unit via the lines LN1 and LN2. The basic software of the relay unit 105, which provides its basic functionalities, is stored in a first memory region of a data storage circuit 122, which the microcontroller 121 can access, in order to load at least parts of the basic software in a volatile working memory of the microcontroller 121.

Data transmission between the communication interfaces S1 and S2 occurs in the present example via an inductive coupling via the connection 117 formed by the communication interface S1 of the sensor unit 107 and the communication interface S2 of the relay unit 105. At the same time, also energy is transmitted wirelessly to the plug head 129 via this connection 117. This energy is converted in the voltage supply unit VSU1 and changed into a corresponding supply voltage for the individual components. The connection 117 between the plug head 129 and the plug head counterpart 131 can, of course, also be embodied as an optical interface or as a galvanic connection, for example, using a cable connection or a plug connection.

The data memory circuits 112 and 122 include, furthermore, in each case, a second memory region, in which an upload software is stored, which is activatable by the microcontroller 111 of the sensor unit 107, or the microcontroller 121 of the relay unit, as the case may be, by the transmission of a password from the base unit and which is configured to perform a reconfiguration of the basic software of the sensor unit 107, or the relay unit 105, likewise stored in the data memory circuits. Furthermore, in the data storage circuit 112 of the sensor unit, or the data storage circuit 122 of the relay unit 105, specific data associated with the sensor unit can be stored, for example, measured values, including main measured value and secondary measured value, for example, as main measured value, a pH measured value, and, as secondary measured value, the temperature of the medium, calibration data, such as zero point and slope of a transfer function, date/clock time of last calibrating, an identification of the calibration method used, data for the sensor state, the number of calibration cycles already performed, assisting parameters for evaluating condition of the sensor unit, especially for predictive diagnosis, a sensor identification with serial number, an identification of the currently present hardware and software versions, especially the currently present versions of the basic software, information concerning the measuring point, at which the measuring system is being applied, as, for example, a tag number, information concerning the measuring transducer, as, for example, range of measurements or date of first startup.

Figure 3:
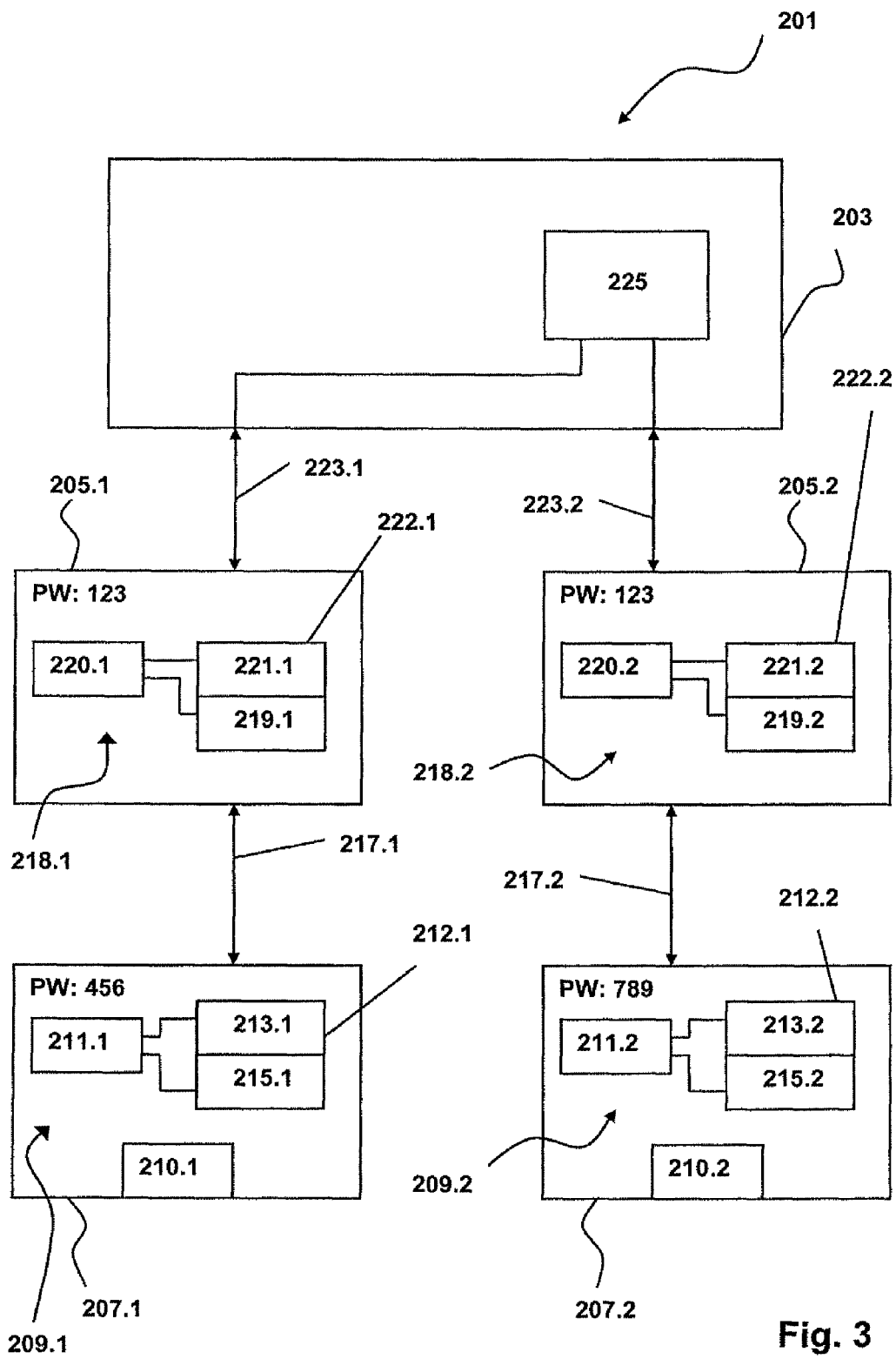
FIG. 3 is a schematic representation of a measuring system having two different sensor units and identically embodied relay units.

FIG. 3 shows, as a further example of an embodiment, a measuring system 201 formed from a base unit 203 and two sensor units 207.1 and 207.2 connected thereto via, respectively, relay units 205.1 and 205.2. The sensor units 207.1 and 207.2 are connected with the relay units 205.1 and 205.2 via interfaces 217.1 and 217.2 for bidirectional data transmission and, in given cases, for the transmission of energy between the base unit 203 and the respective sensor units 207.1 and 207.2. The relay units 205.1 and 205.2 are, in turn, connected via interfaces 223.1 and 223.2 with the base unit for bidirectional data transmission and, in given cases, for the transmission of energy. In detail, the relay units 205.1 and 205.2 can be embodied in the same way as the relay unit 105 presented in FIG. 2.

The first sensor unit 207.1 includes a first measuring transducer 210.1, which produced a signal dependent on a first measured variable, for example, a pH value of the measured medium. The second sensor unit 207.2 includes a second measuring transducer 210.2 different from the first measuring transducer 210.1 for outputting an electrical signal dependent on an additional measured variable of the medium. For example, measuring transducer 210.1 of the first sensor unit 207.1 can be a pH measuring transducer and measuring transducer 210.2 of the second sensor unit 207.2 a conductivity measuring transducer. The sensor units 207.1 and 207.2 comprise, respectively, circuits 209.1 and 209.2, which are formed by at least one microcontroller 211.1 and 211.2 and an associated data memory circuit 212.1 and 212.2. In a first memory region 213.1 of the data storage circuit 212.1 of the first sensor unit 207.1 is stored a basic software, which provides basic functionalities of the first sensor unit 207.1. Correspondingly, in a first memory region 213.2 of the data storage circuit 212.2 of the second sensor unit 207.2 is stored a basic software, which provides basic functionalities of the second sensor unit 207.2. Since the two sensor units 207.1 and 207.2 serve for measuring different measured variables of the measured medium, their basic software is, in each case, differently embodied, i.e. different basic functionalities are provided, in each case, by the basic software.

Furthermore, in a second memory region 215.1 of the data storage circuit 212.1 of the first sensor unit 207.1, an upload software is stored, which can be executed by the microcontroller 211.1 of the first sensor unit 207.1 for updating the basic software of the first sensor unit 207.1 stored in the first memory region 213.1. Correspondingly, in a second memory region 215.2 of the data storage circuit 212.2 of the second sensor unit 207.2 is stored an upload software, which can be executed by the microcontroller 211.2 of the second sensor unit 207.2 for updating the basic software of the second sensor unit 207.2 stored in the first memory region 213.2. It should be pointed out that the sensor units 207.1 and 207.2 can be identically embodied, especially as described in connection with FIG. 1, or FIG. 2.

Via interfaces 217.1 and 217.2, the sensor units 207.1 and 207.2 are, in each case, connected with a relay unit 205.1 and 205.2. The relay units 205.1 and 205.2 can be identically embodied, as described for relay unit 5 with respect to FIG. 1, i.e. they can each comprise a circuit 222.1 and 222.2 having at least one microcontroller 220.1 and 220.2 and at least one data storage circuit 222.1 and 222.2. In a first memory region 219.1 and 219.2 of the data memory circuits 222.1 and 222.2, a basic software is stored, which provides the basic functionalities of the relay units 205.1, or 205.2. In a second memory region 221.1, 221.2 of the data storage circuit 222.1, 222.2 is stored an upload software, by means of which the microcontroller 220.1, 220.2 can perform an updating of the basic software of the relay unit 205.1, 205.2, when activated for execution by the microcontroller 220.1, 220.2 based on a comparison of a data sequence sent from the base unit 203 with a password assigned to the relay unit 205.1, or 205.2, formed, likewise, by a data sequence. The relay units 205.1 and 205.2 are connected with the base unit 203 via interfaces 223.1 and 223.2, respectively. With the interfaces 223.1 and 223.2, data and energy can be transmitted in both directions. The interfaces 223.1 and 223.2 can especially be formed by cable connections.

Assigned to the relay units 205.1 and 205.2 for activating their upload softwares is, in each case, a password formed by a data sequence '123'. Since the two relay units 205.1 and 205.2 in the present example are embodied identically and also have identical basic softwares, the two relay units 205.1 and 205.2 can be assigned the same data sequence '123' as password. The sensor units 207.1 and 207.2 are, in contrast, differently embodied in the present example; especially, they have different basic software types. Correspondingly, they are assigned different passwords. The password of the first sensor unit 207.1 is formed by a first data sequence '456', while the password of the second sensor unit 207.2 is, in contrast, formed by a second data sequence '789'.

In order, for example, selectively to update the basic software of the first sensor unit 207.1, the base unit 203 sends, following start up of the microcontrollers 220.1 and 211.1 of the first sensor unit 207.1 and the first relay unit 205.1, the data sequence '456' to the first relay unit 205.1 connected with the first sensor unit. The microcontroller 220.1 of the relay unit 205.1 performs a comparison between the data sequence '456' received from the base unit with the password assigned to the first relay unit, stored in a memory region of the data storage circuit 222.1, and formed by the data sequence '123'. Since no agreement is present, the data sequence '456' is not recognized as a password. The microcontroller 220.1 then activates the basic software, which is stored in the first memory region 219.1 of the first relay unit 205.1. The first relay unit 205.1 remains, thus, in its basic function operation, in which it forwards all data received from the base unit 203, and, correspondingly, also the data sequence '456', to the first sensor unit 207.1.

The microcontroller 211.1 of the first sensor unit 207.1 compares the data sequence '456' received from the first relay unit 205.1 with the password assigned to the first sensor unit 207.1 stored in a memory region of the data storage circuit 212.1 of the first sensor unit 207.1 and formed by the data sequence '456'. Since agreement is present, the data sequence '456' is recognized as a password. This password recognition initiates an activating of the upload software of the sensor unit 207.1 for execution by the microcontroller 211.1. A software module sent from the base unit 203 via the first relay unit 205.1 to the first sensor unit 207.1 can then be written, with execution of the upload software, at least partially into the first memory region 213.1 of the first sensor unit 207.1, especially with at least partial write over of the basic software previously stored there. After termination of the updating, the microcontroller 211.1 of the first sensor unit 207.1 activates the updated basic software and executes such.

In corresponding manner, the base unit 203 can, by sending the data sequence '789', selectively initiate an activating of the upload software of the second sensor unit 207.2, while the relay units 205.1, 205.2 and the second sensor unit 207.1 remain in their basic function. A software module sent from the base unit 203 can then, with execution of the upload software by the microcontroller 211.2 of the second sensor unit 207.2, be written at least partially into the first memory region 213.2 of the second sensor unit 207.2.

For initiating the updating of the basic software of the relay units 205.1 and 205.2, the base unit 203 sends the data sequence '123' to the relay units 205.1 and 205.2. Since these are constructed identically and use identical basic software, they can be activated simultaneously by the sending of the password, so that their microcontrollers 220.1 and 220.2 essentially with execution of the update software and application of at least one software module sent from the base unit, perform an updating of the basic software in manner analogous to that described for the sensor units 207.1 and 207.2.

The invention claimed is:

1. A measuring system for determining a value of a physical or chemical, measured variable of a medium, comprising:
   a base unit, at least one relay unit connected with said base unit; and
   a sensor unit connected with said relay unit, wherein:
   said relay unit especially is embodied, to receive from said base unit, and to forward to said sensor unit, data, especially measurement data, operating data, commands or software modules, and/or to receive from said sensor unit and to forward to said base unit, data, especially measurement data, operating data, commands or software modules;
   said sensor unit comprises a circuit having at least one microcontroller,
   said sensor unit includes a measuring transducer, which is contactable with the medium, and which outputs an electrical signal dependent on the value of the measured variable;
   said circuit of said sensor unit includes an A/D converter for producing digital data from the electrical signal of said measuring transducer for processing by said microcontroller of said sensor unit;
   said measuring transducer is connected fixedly with a first element of a pluggable connector coupling and said circuit of said sensor unit is accommodated in said first element;
   said relay unit includes a second element of the pluggable connector coupling, and said circuit of said relay unit is accommodated in said second element;
   between said circuit of said sensor unit and said circuit of said relay unit, data and/or enemy are exchangeable via said pluggable connector coupling, when said first and said second elements of said pluggable connector coupling are connected with one another;
   the pluggable connector coupling provides galvanic isolation between the sensor unit and the relay unit by transmitting data and/or energy via an inductive or optical coupling between the circuit of the sensor unit and the circuit of the relay unit;
   said sensor unit comprises at least a first memory region, especially a non volatile, first memory region, in which a firmware of said sensor unit is stored, and a second memory region, especially a non volatile, second memory region, in which an upload software of said sensor unit is stored;
   said upload software of said sensor unit is embodied, in interaction with said at least one microcontroller, to perform an updating of said firmware of said sensor unit with at least one software module provided from said base unit;
   said relay unit comprises a circuit having at least one microcontroller and at least a first memory region, especially a non volatile, first memory region, in which a firmware of said relay unit is stored, characterized in that the circuit of said relay unit further comprises a second memory region, especially a non volatile, second memory region, in which an upload software of said relay unit is stored, which is embodied, in interaction with said at least one microcontroller of said relay unit, to perform an updating of the firmware of said relay unit with at least one software module provided from said base unit; and
   said upload software of said sensor unit, for execution by said microcontroller of said sensor unit, is activatable based on a comparison of a data sequence sent from said base unit with a first password assigned to said sensor unit, especially a first password formed by a first data sequence, and said upload software of said relay unit, for execution by said at least one microcontroller of said relay unit, is activatable based on a comparison of a data sequence sent from said base unit with a second password assigned to said relay unit, especially a second password formed by a second data sequence, especially a second password different from the first password, to selectively execute said upload software of said sensor unit or said upload software of said relay unit.

2. The measuring system as claimed in claim 1, wherein:
said first and the second passwords supplementally serve for verifying authorization of said base unit to perform updates of said firmware of said sensor unit and/or said relay unit.

3. The measuring system as claimed in claim 1, wherein:
said base unit is connected with at least one additional relay unit, which is connected with an additional sensor unit;
said additional relay unit is especially embodied to receive from said base unit, and to forward to said additional sensor unit, data, especially measurement data, operating data, commands or software modules, and/or to receive from said additional sensor unit, and to forward to said base unit, data, especially measurement data, operating data, commands or software modules;
said additional sensor unit comprises a circuit having a microcontroller, at least a first memory region, in which a firmware of said additional sensor unit is stored, and a second memory region, in which an upload software of said additional sensor unit is stored, which is embodied, in interaction with said microcontroller of said additional sensor unit, to perform an updating of the firmware of said additional sensor unit with software modules received from said base unit;
said additional relay unit comprises a circuit having a microcontroller, a first memory region, in which a firmware of said additional relay unit is stored, and a second memory region, in which an upload software of said additional relay unit is stored, which is embodied, in interaction with said microcontroller of said additional relay unit, to perform an updating of the firmware of said additional relay unit; and said upload software of said additional sensor unit, for execution by said microcontroller of said additional sensor unit, is activatable based on a comparison of a data sequence sent from said base unit with a third password assigned to said additional sensor unit, especially a third password different from the first password assigned to said sensor unit.

4. The measuring system as claimed in claim 3, wherein:
the same password is assigned to the upload software of said relay unit and to the upload software of said additional relay unit, so that the upload software of said relay unit is activatable for execution by said microcontroller of said relay unit and the upload software of said additional relay unit is activatable for execution by said microcontroller of said additional relay unit especially simultaneously based on one and the same data sequence sent from said base unit.

5. A method for operation of a measuring system for determining a value of a physical or chemical, measured variable of a medium, especially for start up or updating of the measuring system, wherein the measuring system includes a base unit, at least one relay unit connected with the base unit and a sensor unit connected with the relay unit; wherein
said sensor unit comprises a circuit having at least one microcontroller;
said sensor unit includes a measuring transducer, which is contactable with the medium, and which outputs an electrical signal dependent on the value of the measured variable;
said circuit of said sensor unit includes an A/D converter for producing digital data from the electrical signal of said measuring transducer for processing by said microcontroller of said sensor unit;
said measuring transducer is connected fixedly with a first element of a pluggable connector coupling and said circuit of said sensor unit is accommodated in said first element;
said relay unit includes a second element of the pluggable connector coupling, and said circuit of said relay unit is accommodated in said second element; and
between said circuit of said sensor unit and said circuit of said relay unit, data and/or energy are exchangeable via said pluggable connector coupling, when said first and said second elements of said pluggable connector coupling are connected with one another,
wherein the pluggable connector coupling provides galvanic isolation between the sensor unit and the relay unit by transmitting data and/or energy via an inductive or optical coupling between the circuit of the sensor unit and the circuit of the relay unit; comprising the steps of:
embodying the relay unit to receive from the base unit, and to forward to the sensor unit, data, especially measurement data, operating data, commands or software modules, and/or to receive from the sensor unit, and to forward to the base unit, data, especially measurement data, operating data, commands or software modules;
initiating with the base unit, an updating of firmware of the sensor unit stored in a first memory region of the sensor unit or of firmware of the relay unit stored in a first memory region of the relay unit, and sending to the relay unit a data sequence forming a password;
comparing using a microcontroller of the relay unit, the data sequence with a password assigned to the relay unit, and, in case the data sequence agrees with the password assigned to the relay unit, activating an upload software stored in a second memory region of the relay unit for performing a selective updating of the firmware of the relay unit, or, in case the data sequence does not agree with the password assigned to the relay unit, forwarding by means of a function provided by the firmware of the relay unit, the data sequence to the sensor unit; and
in case the relay unit forwards the data sequence to the sensor unit, a microcontroller of the sensor unit compares the data sequence with a password assigned to the sensor unit, and in case the data sequence agrees with the password assigned to the sensor unit, activates an upload software stored in a second memory region of the sensor unit for performing a selective updating of the firmware of the sensor unit.

6. The method as claimed in claim 5, wherein:
in case the data sequence does not agree with the password assigned to the sensor unit, the microcontroller of the sensor unit executes the firmware of the sensor unit, especially in order to register measured values of the physical or chemical, measured variable and to transmit such to the relay unit.

7. The method as claimed in claim 5, wherein:
sending, using the base unit, for performing the updating of the firmware of the relay unit, at least one software module to the relay unit; and
executing, using the microcontroller of the relay unit, the activated upload software, in order to load the software module received from the base unit at least partially into a third memory region of the relay unit and/or in order to write the software module received from the base unit at least partially into the first memory region of the relay unit, in which the firmware of the relay unit is stored, especially with write over of at least a part of the stored firmware, in order to update the firmware of the relay unit.

8. The method as claimed in claim 5, wherein:
sending, using, the base unit, for performing the updating of the firmware of the sensor unit, sends at least one software module via the relay unit to the sensor unit; and
executing, using the microcontroller of the sensor unit, the activated upload software, in order to load the software module received from the base unit at least partially into a third memory region of the sensor unit and/or in order to write the software module received from the base unit at least partially into the first memory region of the sensor unit, especially with write over of at least a part of the firmware in the first memory region.

9. The method as claimed in claim 5, wherein:
starting up the microcontroller of the sensor unit for initiating the updating of the sensor unit, and in case it receives from the base unit, within a predetermined time span, forwarded via the relay unit, a data sequence, which agrees with the password assigned to the sensor unit, activating the upload software stored in the second memory region of the sensor unit in such a manner, that the upload software is executable by means of the microcontroller, in order to update the firmware of the sensor unit; and
the microcontroller of the sensor unit otherwise activates the firmware stored in the first memory region of the sensor unit in such a manner, that the firmware is executable by means of the microcontroller, in order to derive a measured value from a signal of a measuring transducer of the sensor unit supplied to the microcontroller via an A/D converter and to transmit such measured value to the relay unit.

10. The method as claimed in claim 5, wherein:
starting up the microcontroller of the relay unit for initializing the updating of the relay unit, and, in case it receives from the base unit, within a predetermined time span, a data sequence, which agrees with the password assigned to the relay unit, activating the upload software stored in the second memory region of the relay unit in such a manner, that the upload software is executable by means of the microcontroller, in order to update the firmware of the relay unit; and the microcontroller of the relay unit otherwise activates the firmware stored in the first memory region of the relay unit in such a manner, that the firmware is executable by means of the microcontroller, in order to receive from the base unit, and to forward to the sensor unit, data, especially measurement data, operating data, commands or software modules, and/or to receive from the sensor unit, and to forward to the base unit, data, especially measurement data, operating data, commands or software modules.

* * * * *